United States Patent [19]

Murtha

[11] 4,230,638

[45] Oct. 28, 1980

[54] SEPARATION OF CYCLOHEXYLBENZENE FROM A CYCLOHEXYLBENZENE-CYCLOHEXANONE-PHENOL ADMIXTURE

[75] Inventor: Timothy P. Murtha, Bartlesville, Okla.

[73] Assignee: Phillips Petroleum Company, Bartlesville, Okla.

[21] Appl. No.: 36,268

[22] Filed: May 4, 1979

[51] Int. Cl.² .................... C07C 45/24; C07C 7/01
[52] U.S. Cl. .................................... 568/366; 203/43; 585/803; 585/807; 585/857; 568/749
[58] Field of Search ............ 260/586 R, 586 P, 593 P; 203/43; 585/803, 807, 857; 568/749

[56] References Cited

U.S. PATENT DOCUMENTS

| 2,782,242 | 2/1957 | Clark | 260/621 |
| 3,065,169 | 11/1962 | Zuiderweg et al. | 208/321 |
| 3,209,047 | 9/1965 | Young | 260/674 |
| 4,021,490 | 5/1977 | Hudson | 260/586 R |

OTHER PUBLICATIONS

"Handbook of Chemistry and Physics" 50th Ed. (1969-1970), The Chemical Rubber Co., Publ. pp. C-140; C-149; C-258 and C-421.

Primary Examiner—Natalie Trousof
Assistant Examiner—L. Hendriksen

[57] ABSTRACT

Cyclohexylbenzene is separated from a cyclohexylbenzene-cyclohexanone-phenol admixture by liquid-liquid extraction with a non-polar solvent such as hexadecane and a polar solvent, such as sulfolane, diethylene glycol, or mixtures with water. Cyclohexylbenzene is separated from the non-polar phase by fractional distillation. Phenol and cyclohexanone are separated from the polar solvent by fractional distillation.

14 Claims, 1 Drawing Figure

SEPARATION OF CYCLOHEXYLBENZENE FROM A CYCLOHEXYLBENZENE-CYCLOHEXANONE-PHENOL ADMIXTURE

FIELD OF THE INVENTION

The invention pertains to the separation of cyclohexylbenzene from cyclohexylbenzene-cyclohexanone-phenol mixture.

BACKGROUND OF THE INVENTION

Both phenol and cyclohexanone can be produced from cyclohexylbenzene. For example, cyclohexylbenzene is oxidized to cyclohexylbenzene hydroperoxide, and the latter then subsequently cleaved to produce phenol and cyclohexanone. In a typical reaction, the cyclohexylbenzene conversion in the oxidation step is in the range of about 15 to 25 weight percent, which helps to minimize side reactions while maintaining high selectivity to cyclohexylbenzene hydroperoxide. It is not feasible, though, to remove cyclohexylbenzene hydroperoxide from the reaction product stream because of its chemical reactivity and thermal instability. Thus, the cyclohexylbenzene hydroperoxide must be cleaved to phenol and cyclohexanone before separations are attempted.

The resulting admixture of cyclohexylbenzene, phenol, and cyclohexanone, however, is difficult to separate even by distillation techniques because phenol and cyclohexanone form a maximum boiling azeotrope of about 72:28 weight percent boiling at about 184° C. at substantially atmospheric pressure, and therefore cannot suitably be separated by fractionation. In addition, cyclohexylbenzene appreciably codistills with the azeotrope, resulting in additional separation problems.

To make the production scheme of cyclohexylbenzene to phenol and cyclohexanone viable, methods must be found to adequately separate out the cyclohexylbenzene for recycle.

BRIEF DESCRIPTION OF THE INVENTION

I have discovered that cyclohexylbenzene can be removed from a mixture of cyclohexylbenzene, phenol, and cyclohexanone by an extraction process. My extraction process utilizes a hydrocarbon solvent plus one or other of a selected polar solvent, optionally with a small amount of water.

BRIEF DESCRIPTION OF THE DRAWING

In my FIGURE I attached, a feed admixture 1 of cyclohexylbenzene CHB, phenol, and cyclohexanone is taken to an extraction step 2 for contact with polar solvent 3 and hydrocarbon 4. Usually this contacting step 2 also receives a recycle stream of cyclohexylbenzene-phenol-cyclohexanone 17 obtained as described hereinafter.

The extraction admixture 5 is separated 6, forming a polar phase 7 comprising polar solvent, phenol, and cyclohexanone; and a hydrocarbon phase 8 containing hydrocarbon solvent, cyclohexylbenzene, and some amounts of phenol and cyclohexanone.

Figure 1:
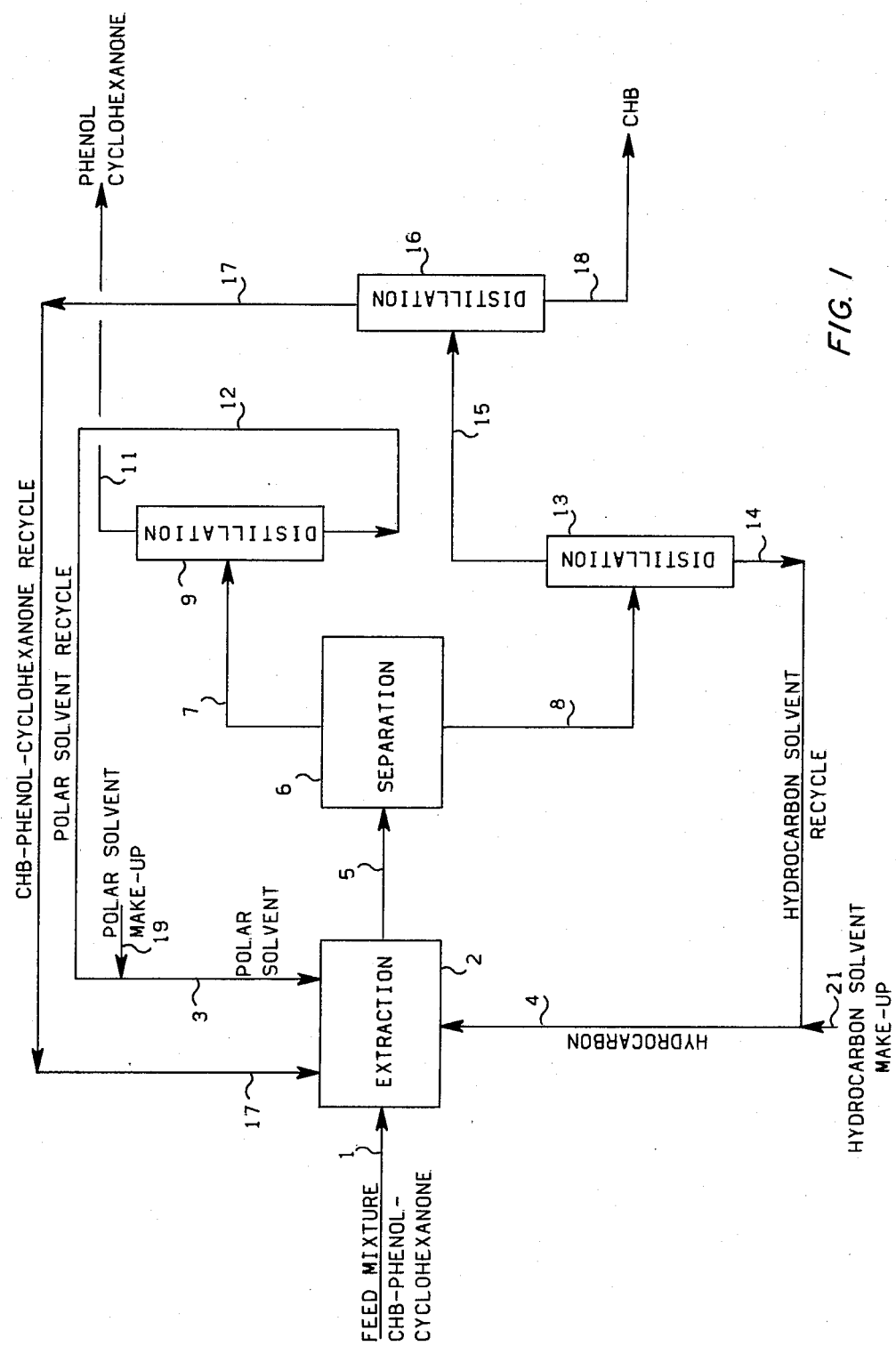

The polar phase 7 containing polar solvent, phenol, and cyclohexanone, is taken to distillation 9. Distillation 9 produces overhead stream 11 containing phenol and cyclohexanone substantially free of cyclohexylbenzene, and bottoms 12 of separated polar solvent. The separated polar solvent 12 can be augmented by polar solvent makeup 19, as may be necessary, for recycle 3 to the extraction step 2.

The hydrocarbon phase 8 from separation 6 contains hydrocarbon solvent, cyclohexylbenzene, and some phenol and cyclohexanone. This phase is distilled 13 to produce bottoms 14 which primarily is hydrocarbon separated hydrocarbon solvent, and overhead 15 which is a mixture of phenol, cyclohexanone, and cyclohexylbenzene. The separated hydrocarbon solvent 14 can be augmented with hydrocarbon solvent makeup 21, as may be necessary, for recycle 4 to the extraction step 2. The overhead 15, containing phenol, cyclohexanone, and cyclohexylbenzene, is taken to a further distillation step 16. Distillation 16 produces an overhead 17 of cyclohexylbenzene, phenol, cyclohexanone for recycle back to the extraction step 2, and bottoms 18 of substantially pure cyclohexylbenzene which can be recycled to the initial oxidation step (not shown). In order to simplify the figure, conventional items of equipment such as pumps, drains, valves, reflux lines, recording and controlling instruments, and the like are not included.

DETAILED DESCRIPTION OF THE INVENTION

Extraction Process

The extraction process of my invention provides a method of first separating cyclohexylbenzene (CHB) from a CHB-phenol-cyclohexanone mixture to yield a simpler two-component mixture containing phenol and cyclohexanone substantially free of CHB.

The feed mixture to be separated is contacted with a polar solvent and a hydrocarbon solvent under liquid-liquid extraction conditions to form two phases, followed by separation of the two phases.

The polar phase, which contains the polar solvent, phenol, and cyclohexanone, is processed to separate the polar solvent for recycling, and the desired phenol-cyclohexanone mixture. The hydrocarbon phase, which contains the hydrocarbon solvent, CHB, phenol, and cyclohexanone, is separated to recover the hydrocarbon solvent for recycle to the extraction stage and to recover the CHB. The accompanying FIGURE illustrates the process of my invention.

Obviously, numerous variations are possible within the process. For example, the mixture to be separated can be premixed with the polar solvent before entering the extraction vessel. Also, the extraction and separation can be carried out in the same vessel. Although preferred are hydrocarbon solvents boiling higher than the mixture components, hydrocarbon solvents boiling lower than the mixture components can be utilized with the solvents becoming the overhead stream or first fraction and the components being the bottoms stream or later fractions in distillation column 13. The distillations can be batch or continuous distillations. When water is present in the polar solvent, the phenol-cyclohexanone overhead may contain water.

In the practice of the process of my invention, any mixture of phenol, cyclohexanone, and cyclohexylbenzene can be used as the feed mixture to be separated. It is within the scope of my invention to preremove by suitable methods a portion of any of the components from the mixture to be separated before the extraction process of my invention. For example, any excess of cyclohexanone over the quantity represented in the azeotrope can be first distilled from the mixture as an essentially pure material. Since cyclohexylbenzene codistills with the phenol-cyclohexanone azeotrope in quantities of about 2 to 10 weight percent, any excess of cyclohexylbenzene over that amount can be separated by fractional distillation by taking the phenol-cyclohexanone mixture containing about 2 to 10 weight percent cyclohexylbenzene overhead.

Hydrocarbon Solvent

The hydrocarbon solvent utilized in the extraction process of my invention is an acyclic or cyclic saturated hydrocarbon containing about 5 to 25 carbon atoms per molecule. The hydrocarbon solvent can be either one hydrocarbon, or a mixture of two or more hydrocarbons.

For ease of separation of solvent and extracted materials without requiring large energy consumption in the distillation of large volumes of solvent, as well as for ease of handling, the currently preferred hydrocarbon solvents have boiling points above about 250° C. and are liquids at the extraction temperatures employed.

Examples of suitable solvents include such as pentane, hexane, heptane, octane, nonane, decane, undecane, dodecane, tetradecane, pentadecane, hexadecane, heptadecane, octadecane, nonadecane, eicosane, pentacosane, 2-methylpentane, 3-methyloctane, 2-methylpentadecane, 2,2,6,6,7-pentamethyloctane, 3-ethyl-2,6-dimethylheptane, cyclohexane, cyclodecane, cyclohexadecane, 1,2-diethylcyclooctane, and the like, and mixtures thereof.

Polar Solvent

The polar solvent utilized in the process of my invention is selected from compounds of general formula I:

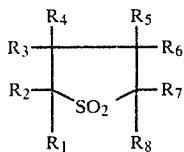

or compounds of general formula II:

and mixtures of compounds of formulas I or II with water.

In each formula (I) and (II), $R_1$, $R_2$, $R_3$, $R_4$, $R_5$, $R_6$, $R_7$, $R_8$, and $R_9$ each is individually selected from hydrogen and alkyl radicals containing 1 to 10 carbon atoms per radical, and n is an integer of 2 to 5. The mixtures of compounds of general formula (I) with water can contain up to as much as about 60 weight percent water; mixtures of compounds of general formula (II) with water can contain up to as much as about 85 weight percent water.

For reasons of availability, the preferred polar solvents for use in the process of my invention are compounds of general formula (I), mixtures of compounds of general formula (I) with up to about 60 weight percent water, compounds of general formula (II), and mixtures of compounds of general formula (II) with up to about 85 weight percent water, wherein each of $R_1$, $R_3$, $R_5$, and $R_7$ is hydrogen, each of $R_2$, $R_4$, $R_6$, $R_8$, and $R_9$ is selected from hydrogen or alkyl radicals containing 1 to 4 carbon atoms per radical, and n is an integer of 2 to 4.

For reasons of availability and cost, the currently most preferred polar solvents for use in the extraction process of my invention are compounds of the general formula (I), mixtures of compounds of general formula (I) with up to about 40 weight percent water, compounds of general formula (II), and mixtures of compounds of general formula (II) with up to about 55 weight percent water, wherein each of $R_1$ to $R_8$ is hydrogen, $R_9$ is hydrogen or methyl, and n is an integer of 2 to 4.

Examples of polar solvents suitable for use in my invention include sulfolane (tetrahydrothiophene-1,1-dioxide), 2-methylsulfolane, 3-methylsulfolane, 2,5-dimethylsulfolane, 2,3,4,5-tetramethylsulfolane, 2,2-dimethylsulfolane, 2-ethylsulfolane, 2-butylsulfolane, 2-decylsulfolane, diethylene glycol (3-oxapentane-1,5-diol), triethylene glycol (3,6-dioxaoctane-1,8-diol), 3,6,9,12-tetraoxatetradecane-1,14-diol, dipropylene glycol (2-methyl-3-oxahexane-1,5-diol), 2,5-dimethyl-3,6-dioxanonane-1,8-diol, 2-octyl-3-oxatridecane-1,5-diol, and the like, and mixtures, and mixtures of these compounds with water.

Extraction Conditions

The extraction process of my invention can be carried out in any batch or continuous manner that accomplishes the desired separation. Examples of various batch and continuous extraction equipment are found in R. H. Perry and C. H. Chilton *Chemical Engineers' Handbook*, 5th Ed., (McGraw-Hill Book Co., N.Y. 1973) sections 21-3 to 21-29.

The temperature utilized in the extraction process of my invention can be any temperature that allows the desired degree of separation to occur. In general, the temperature will be in the range of about 0° to 130° C., with the lower limit being determined by economic and freezing point considerations, and the upper limit being determined by economic considerations and the desire to avoid possible thermal side reactions. For reasons of economics and ease of handling, the preferred temperature range is about 10° C. to 60° C.

The pressure utilized in the extraction process can be atmospheric or superatmospheric, although for conversion of operation, atmospheric pressure is preferred.

As in most extraction processes, intimate contact of the two phases is desired and can be accomplished by the design of the extraction equipment, e.g., in a countercurrent extraction, or by added stirrers, mixers, or agitators.

The amount of polar solvent utilized in the process of my invention can be expressed as a weight ratio of feed mixture to be separated:polar solvent. Broadly, this weight ratio can range from about 1:100 to 200:100, preferably about 10:100 to 100:100.

Although the weight ratio of hydrocarbon solvent:polar solvent will depend somewhat on the specific equipment utilized and on the degree of separation desired, it generally will range from about 10:100 to 1000:100, preferably about 50:100 to 500:100.

EXAMPLES

In the following examples, the solvents, phenol, and cyclohexanone were commercially available materials and were used without further purification. The cyclohexylbenzene (CHB) was prepared by the reductive alkylation of benzene.

EXAMPLE I

Three runs were carried out in which cyclohexylbenzene (CHB) was removed from a CHB-phenol-cyclohexanone mixture by liquid-liquid extraction with hexadecane and either diethylene glycol (DEG) or aqueous DEG. In each run, a 500 ml separatory funnel was charged with 50 g of a mixture containing 10 weight percent CHB, 63 weight percent phenol, and 27 weight percent cyclohexanone and with 150 g of the DEG or the aqueous DEG. This mixture was extracted four times with 50 ml (38.6 g) portions of hexadecane. Each of the hexadecane extracts was analyzed by gas-liquid chromatography (glc). The results of the analyses are shown in Table I:

TABLE I

| | Polar Sol. | | | Present in Hexadecane Extract[a] | | | CHB Removed[b] | | CHB Recovered[c] | |
|---|---|---|---|---|---|---|---|---|---|---|
| | DEG, | H$_2$O | Wt., | Wt. % | | | | | | |
| Run | g | g | g | CHB | PhOH | Cyclo-hexanone | g | Wt. % | g | Wt. % |
| 1 | 150 | 0 | 6.9 | 71.6 | 3.2 | 25.2 | 4.91 | 98.3 | 4.87 | 97.4 |
| 2 | 127.5 | 22.5 | 8.3 | 59.5 | 7.1 | 33.3 | 4.93 | 98.7 | 4.84 | 96.8 |
| 3 | 75 | 75 | 13.3 | 37.5 | 14 | 48.5 | 5 | 100 | 4.7 | 94 |

[a] Compounds present in the combined hexadecane extracts expressed as the total weight present and as a weight percent of the total.
[b] Amount of CHB removed from the original mixture. The weight percent is based on the 5 g present in the original mixture.
[c] Calculated amount of CHB recovered from distillation of the compounds present in the hexadecane extracts. The weight percent is based on the 5 g present in the original mixture.

The results presented in Table I show that a liquid-liquid extraction with hexadecane and DEG or aqueous DEG removes over 98 weight percent of the CHB from a CHB-phenol-cyclohexanone mixture. Distillation of the compounds present in the combined hexadecane extracts is calculated using previously determined distillation data to contain 94 weight percent or more of the CHB present in the original mixture. Only about 1 weight percent hexadecane, based on the total polar phase weight, was present in the polar phase in Run 1. No detectable (by glc) amount of hexadecane was present in the polar phase in Runs 2 and 3.

EXAMPLE II

Four runs were carried out in which CHB was removed from a CHB-phenol-cyclohexanone mixture by liquid-liquid extraction with hexadecane and either sulfolane or aqueous sulfolane. In each run, a 500 ml separatory funnel was charged with 50 g of a mixture containing 10 weight percent CHB, 63 weight percent phenol, and 27 weight percent cyclohexanone, and with 100 g of the sulfolane or the aqueous sulfolane. The resulting mixture was extracted four times with 50 ml (38.6 g) portions of hexadecane. Each of the hexadecane extracts was analyzed by glc. The results of these Runs are shown in Table II:

TABLE II

| | Polar Solvent | | | Present in Hexadecane Extract | | | CHB Removed | | CHB Recovered | |
|---|---|---|---|---|---|---|---|---|---|---|
| | Sulfolane | H$_2$O | Wt., | Wt. % | | | | | | |
| Run | g | g | g | CHB | PhOH | Cyclo-hexanone | g | Wt. % | g | Wt. % |
| 4 | 100 | 0 | 7.2 | 65.1 | 6.4 | 28.5 | 4.69 | 93.9 | 4.62 | 92.4 |
| 5 | 90 | 10 | 7.1 | 68.9 | 5.8 | 25.4 | 4.91 | 98.2 | 4.85 | 97 |
| 6 | 80 | 20 | 7.2 | 69.6 | 5.2 | 25.2 | 4.98 | 99.5 | 4.92 | 98.4 |
| 7 | 70 | 30 | 7.3 | 66.3 | 7.5 | 26.2 | 4.85 | 97 | 4.76 | 95.2 |

The results in Table II demonstrate the removal of over 93 weight percent of the CHB from a CHB-phenol-cyclohexanone mixture by an extraction with hexadecane and sulfolane or aqueous sulfolane. Distillation of the compounds present in the combined hexadecane extracts is calculated to recover 92 weight percent or more of the CHB present in the original mixture. Less than about 0.5 weight percent hexadecane, based on the total polar phase weight, was present in the polar phase in each run.

EXAMPLE III

A control run was carried out to demonstrate the importance of the polar solvent in the removal of CHB from a CHB-phenol-cyclohexanone mixture by making an extraction using only hexadecane. In control Run 8, a separatory funnel was charged with 50 g of a mixture containing 10 weight percent CHB, 63 weight percent phenol, and 27 weight percent cyclohexanone. This mixture was extracted four times with 50 ml (38.6 g) portions of hexadecane. The hexadecane extracts were each analyzed by glc. The results of this Run are shown in Table III:

TABLE III

| | | | Present in Hexadecane Extract | | | CHB Removed | | CHB Recovered | |
|---|---|---|---|---|---|---|---|---|---|
| Run | Polar Solvent | Wt. g | CHB | PhOH | Cyclo-hexanone | g | Wt. % | g | Wt. % |
| 8 | none | 18.8 | 25.6 | 49.8 | 24.6 | 4.83 | 96.5 | 3.33 | 66.6 |

The results of this control Run 8 show that an extraction with hexadecane but without an added polar solvent does remove a high percentage of the CHB from the starting mixture, but also removes large and undesirable quantities of phenol. Thus, the extraction removed 9.36 g of phenol, which is 30 weight percent of the amount of phenol present in the starting mixture. In contrast, the inventive Runs 1 to 2 and 4 to 7 removed less than 2 weight percent of the phenol present in the starting mixture while inventive Run 3 removed 6 weight percent phenol.

EXAMPLE IV

Several control runs were carried out to show several polar solvents that are less suitable for use in the removal of CHB from a CHB-phenol-cyclohexanone mixture than the polar solvents of my invention.

In control Run 9, 55 g of a mixture containing 9.1 weight percent CHB, 33.6 weight percent cyclohexanone, and 57.3 weight percent phenol was mixed with 100 g of dimethyl formamide (DMF) and extracted four times with 50 ml (38.6 g) portions of hexadecane. A glc analysis of the hexadecane extracts showed that only 73.4 weight percent of the CHB in the starting mixture had been removed.

In each of control Runs 10 and 11, 50 g of a mixture containing 10 weight percent CHB, 63 weight percent phenol, and 27 weight percent cyclohexanone was used.

In control Run 10, the mixture was added to 150 ml of methanol and extracted four times with 50 ml (38.6 g) portions of hexadecane. A glc analysis of the hexadecane extracts and of the methanol phase showed that about 90.5 weight percent of the CHB in the starting mixture had been extracted, but also that the methanol phase contained about 9 weight percent hexadecane. In all of the inventive Runs 1 and 7, the polar phase of the extraction contained less than 1 weight percent hexadecane.

In control Run 11, the mixture described above was added to 150 ml of glycerol and extracted four times with 50 ml (38.6 g) portions of hexadecane. The last extraction involved heating the mixture to 90° C. with stirring before separation. A glc analysis of both the hexadecane extracts and the glycerol layer showed that considerable amounts of ketal formed from glycerol and cyclohexanone were present in the glycerol phase. Identification of the ketal was made by comparison with an independently prepared sample. The results of this control Run 11 demonstrated that polar solvents containing the 1,2-diol feature should be avoided to prevent ketal formation with cyclohexanone.

In control Run 12, 100 g of a mixture containing 80 weight percent CHB, 10 weight percent phenol, and 10 weight percent cyclohexanone was extracted three times with 100 g portions of water with heating to 70° C. and stirring. A glc analysis of each water extract and of the organic layer indicated that all three components of the original mixture were present in both the water layers and in the organic layers.

The results of control Runs 9 through 12 show that DMF, methanol, glycerol, and water are significantly less effective or less desirable than the solvents of my invention for the removal of CHB from a CHB-phenol-cyclohexanone mixture.

EXAMPLE V

Another inventive run was carried out to demonstrate the separation process of my invention using pentane as the hydrocarbon solvent. In Run 13, 50.5 g of a mixture containing 63.6 weight percent phenol, 27.2 weight percent cyclohexanone, and 9.1 weight percent CHB, and 75 ml (83.9 g) of diethylene glycol was charged to a separatory funnel. To this mixture was added 40 ml water, with mixing two phases formed. The upper layer was removed and an additional 20 ml of water was added to the bottom layer. Again two phases formed and the top layer was separated. The bottom layer was extracted with two 50 ml (31.3 g) portions of pentane. The pentane extracts were dried over $MgSO_4$, filtered, and concentrated under reduced pressure on a rotary evaporator to leave a residue. A glc analysis of the remaining polar layer indicated that the CHB had been essentially completely removed from the mixture. Distillation of the combination of the two phases initially separated and the residue from the pentane extract is calculated to recover 91 weight percent of the CHB present in the original mixture.

The results of Run 13 demonstrate that the separation of my invention can be carried out using pentane as the hydrocarbon solvent.

EXAMPLE VI

Other attempts at extractive separation were made. For example, extraction was attempted with 1,2,6-hexanetriol, but was terminated when ketal formation between cyclohexanone and glycerol was discovered, since it was anticipated that ketal formation also would occur with 1,2,6-hexanetriol.

This disclosure, including data, illustrate the value and effectiveness of my invention. The examples, the knowledge and background, the field of the invention, and general principles of chemistry and of other applicable sciences have formed the bases from which the broad description of the invention including the ranges of conditions and generic groups of operant components have been developed, which, in turn, have formed the bases for my claims here appended.

I claim:

1. A process for the separation of an admixture of cyclohexylbenzene, phenol, and cyclohexanone, which comprises:
    (a) contacting said admixture under liquid-liquid extraction conditions with amounts and proportions of at least one nonpolar hydrocarbon solvent and at least one polar solvent effective to produce a two-phase admixture comprising a polar phase comprising said polar solvent and rich in phenol and cyclohexanone, and a hydrocarbon phase comprising said hydrocarbon solvent and rich in cyclohexylbenzene and lean in phenol and cyclohexanone.
wherein said hydrocarbon solvent is selected from acyclic or cyclic saturated hydrocarbons of 5 to 25 carbon atoms per molecule and said polar solvent is:

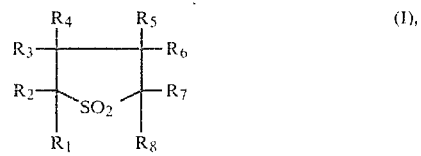

or mixtures of (I) or (II) with water, wherein each of $R_1$, $R_2$, $R_3$, $R_4$, $R_5$, $R_6$, $R_7$, $R_8$, $R_9$, is hydrogen or an alkyl radical of 1 to 10 carbon atoms per radical, and wherein n is an integer of 2 to 5,
    (b) phase separating said two-phase admixture into said polar phase and said hydrocarbon phase, (c) fractionally distilling said polar phase to produce a recycle polar solvent stream, and a first recovery stream of phenol and cyclohexanone, (d) fractionally distilling said hydrocarbon phase to produce a recycle hydrocarbon solvent stream, and a second recovery stream rich in cyclohexylbenzene, and lean in phenol and cyclohexanone, (e) fractionally distilling said second recovery stream to produce a stream of cyclohexylbenzene product, and a recycle stream of residual cyclohexylbenzene, phenol, and cyclohexanone for recycle to said liquid-liquid extraction step, (f) recycling said recycle polar solvent stream to said contacting step (a), (g) recycling said recycle hydrocarbon solvent stream to said contacting step (a), and (h) recycling said residual stream of cyclohexylbenzene, phenol, and cyclohexanone to said contacting step (a).

2. The process according to claim 1 wherein said hydrocarbon solvent is selected from hydrocarbon solvents within the $C_5$–$C_{25}$ carbon range having boiling points above about 250° C. and liquid under extraction conditions.

3. The process according to claim 1 wherein said hydrocarbon solvent is selected from the group consisting of pentane, hexane, heptane, octane, nonane, decane, undecane, dodecane, tetradecane, pentadecane, hexadecane, heptadecane, octadecane, nonadecane, eicosane, pentacosane, 2-methylpentane, 3-methyloctane, 2-methylpentadecane, 2,2,6,6,7-pentamethyloctane, 3-ethyl-2,6-dimethylheptane, cyclohexane, cyclodecane, cyclohexadecane, 1,2-diethylcyclooctane, and mixtures thereof.

4. The process according to claim 1 wherein said polar solvent is said (I) and further contains up to 60 weight percent water.

5. The polar solvent according to claim 1 wherein said polar solvent is said (II) and further contains up to as much as 85 weight percent water.

6. The process according to claim 1 wherein in said polar solvent each of said $R_1$, $R_3$, $R_5$, and $R_7$ is hydrogen; each of $R_2$, $R_4$, $R_6$, $R_8$, $R_9$ is hydrogen or alkyl radical of 1 to 4 carbon atoms per radical, and n is an integer of 2 to 4.

7. The process according to claim 6 wherein in said polar solvent said each of $R_1$ to $R_8$ is hydrogen, $R_9$ is hydrogen or methyl, and n is an integer of 2 to 4.

8. The process according to claim 1 wherein said polar solvent is selected from the group consisting of sulfolane (tetrahydrothiophene-1,1-dioxide), 2-methylsulfolane, 3-methylsulfolane, 2,5-dimethylsulfolane, 2,3,4,5-tetramethylsulfolane, 2,2-dimethylsulfolane, 2-ethylsulfolane, 2-butylsulfolane, 2-decylsulfolane, diethylene glycol (3-oxapentane-1,5-diol), triethylene glycol (3,6-dioxaoctane-1,8-diol), 3,6,9,12-tetraoxatetradecane-1,14-diol, dipropylene glycol, 1,4,7-trimethyl-3,6-dioxaoctane-1,8-diol, 2-octyl-3-oxatridecane-1,5-diol, and mixtures, and mixtures of these compounds with water.

9. The process according to claim 8 wherein said liquid-liquid extraction is conducted at about 0° to 130° C.

10. The process according to claim 9 employing a ratio of about 1:100 to 200:100 weight ratio of polar solvent to feed mixture.

11. The process according to claim 10 employing a weight ratio of hydrocarbon solvent:polar solvent of about 10:100 to about 1000:100.

12. The process according to claim 11 wherein said hydrocarbon solvent is hexadecane, and said polar solvent is diethylene glycol or diethylene glycol plus water.

13. The process according to claim 12 wherein said hydrocarbon solvent is hexadecane, and said polar solvent is sulfolane or sulfolane plus water.

14. The process according to claim 1 wherein said liquid-liquid extraction step is preceded by distillation step to remove any one of cyclohexylbenzene-cyclohexanone-phenol in excess, such that the resulting admixture is substantially an azeotrope of phenol/cyclohexanone with about 2 to 10 weight percent cyclohexylbenzene.

* * * * *

UNITED STATES PATENT AND TRADEMARK OFFICE
CERTIFICATE OF CORRECTION

PATENT NO. : 4,230,638

DATED : October 28, 1980

INVENTOR(S) : Timothy P. Murtha

It is certified that error appears in the above-identified patent and that said Letters Patent are hereby corrected as shown below:

Claim 1, Column 8, line 60, after the formula "(I)" formula "(II)" should be:

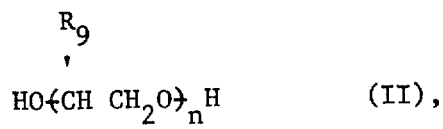

$$HO(CH\overset{R_9}{|}CH_2O)_nH \quad (II),$$

Signed and Sealed this

Third Day of March 1981

[SEAL]

Attest:

Attesting Officer

RENE D. TEGTMEYER

*Acting Commissioner of Patents and Trademarks*